Figure 1:
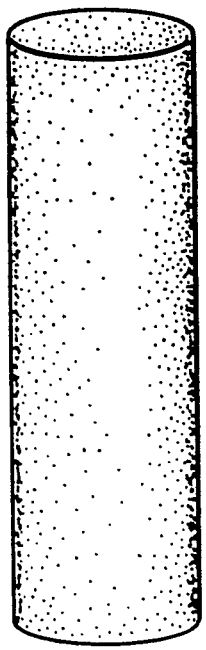

United States Patent [19]

Hornykiewytsch et al.

[11] Patent Number: 5,252,561
[45] Date of Patent: Oct. 12, 1993

[54] PREPARATION FOR THE CONTROLLED RELEASE OF ACTIVE SUBSTANCES WHICH ARE SUITABLE AS A THERAPEUTCS OR FOR IMPROVING GROWTH AND FEED UTILIZATION IN RUMINANTS

[75] Inventors: Theophil Hornykiewytsch, Frankfurt am Main; Dieter Düwel, Hofheim am Taunus, both of Fed. Rep. of Germany

[73] Assignee: Hoechst Aktiengesellschaft, Frankfurt am Main, Fed. Rep. of Germany

[21] Appl. No.: 824,933

[22] Filed: Jan. 24, 1992

[30] Foreign Application Priority Data

Jan. 28, 1991 [DE] Fed. Rep. of Germany ....... 4102395
Apr. 23, 1991 [DE] Fed. Rep. of Germany ....... 4113146

[51] Int. Cl.⁵ .................. A61K 31/70; A61K 31/715; A61K 31/685
[52] U.S. Cl. ........................................ 514/23; 514/57; 514/78; 514/372; 514/393; 514/396; 424/78.18; 424/468; 424/474; 424/476; 424/646
[58] Field of Search ...................... 424/195.1, 468, 474, 424/476, 479, 646, 78.18; 514/78, 396, 23, 57, 393, 372

[56] References Cited

U.S. PATENT DOCUMENTS 3,535,419 10/1970 Siegrist ............................... 424/468

FOREIGN PATENT DOCUMENTS

| | | |
|---|---|---|
| 73757/87 | 12/1987 | Australia . |
| 0025696 | 3/1981 | European Pat. Off. . |
| 0025697 | 3/1981 | European Pat. Off. . |
| 0164241 | 12/1985 | European Pat. Off. . |
| 0243111 | 4/1987 | European Pat. Off. . |
| 0236002 | 9/1987 | European Pat. Off. . |
| 0236901 | 9/1987 | European Pat. Off. . |
| 0284258 | 9/1988 | European Pat. Off. . |
| 0332094 | 9/1989 | European Pat. Off. . |
| 0333311 | 9/1989 | European Pat. Off. . |
| 0385106 | 9/1990 | European Pat. Off. . |
| 0406015A1 | 1/1991 | European Pat. Off. . |
| 2077103 | 12/1981 | United Kingdom . |

OTHER PUBLICATIONS

World Patents Index, Section Ch, Week 8804, Derwent Publications Ltd., London, GB; Class C AN 88-021787 & AU-A-8-773 757 (Rowe J. B. et al.), Dec. 3, 1987.

Primary Examiner—John W. Rollins
Attorney, Agent, or Firm—Curtis, Morris & Safford

[57] ABSTRACT

The invention relates to a composition which contains at least one active substance, a wax, a weighting agent and optionally a sugar, sugar alcohol, cellulose ether or a polyethylene glycol, an active substance release system built up from this composition, a process for its preparation and its use in veterinary medicine and animal nutrition.

41 Claims, 2 Drawing Sheets

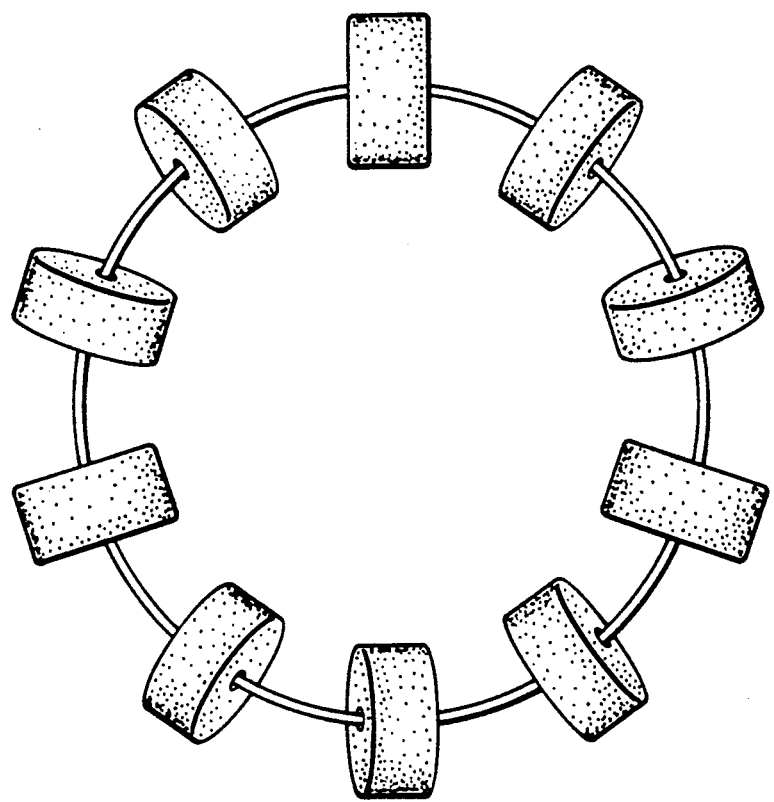

PREPARATION FOR THE CONTROLLED RELEASE OF ACTIVE SUBSTANCES WHICH ARE SUITABLE AS A THERAPEUTCS OR FOR IMPROVING GROWTH AND FEED UTILIZATION IN RUMINANTS

The invention relates to a composition which contains at least one active substance, a wax, a weighting agent and if appropriate a sugar, sugar alcohol, cellulose ether or a polyethylene glycol, an active substance release system composed of this composition, a process for its preparation and its use in veterinary medicine and animal nutrition.

Active substance release systems are preparations which release one or more (physiologically) active constituents in a defined release profile and in a controlled manner over a fixed period of time.

The most important indication areas for the use of these systems in veterinary medicine are:
1) Therapy in the narrower sense, i.e. the control of parasitic infections and/or diseases, and also in the wider sense
2) the supply of deficient substances (for example: trace elements)
3) the control of metabolic processes (for example: performance)
4) the control of endocrine processes (for example: fertility).

Indication areas for use of these systems in animal nutrition are in particular the improvement of growth and feed utilization in ruminants.

Advantages of active substance release systems in comparison with conventional administration forms are an optimum active substance level during the entire administration period, a lower active substance dosage, and a saving of work and thus in the end costs for the livestock owners.

The disadvantages which possibly occur, such as development of resistance or dependence, active substance residues and waiting time, tissue irritations and remainder of a foreign body after the end of administration, can and must be excluded by means of optimum pharmaceutical development or at least distinctly minimized.

Active substance release systems for oral administration in ruminants, called "bolus" in the following, have been described in detail in the specialist literature (for example Formulation of Veterinary Dosage Forms, by Jack Blodinger, Marcel Dekker Inc. New York, 1983). The fact that the bolus remains in the gastrointestinal tract of the animal is caused by the geometric shape or by the density of the system. In the latter case, one speaks of a "high density device" (HDD). It is known from the literature that HDDs should have a density $>2$ g/cm$^3$ (J. Riner et al., Am. J. Vet. Res. 43 (1982), pp. 2028-2030), in order that the bolus cannot be regurgitated again in spite of the natural regurgitation of the ruminants.

The "high density devices" described to date are therefore provided with a weighting component in order to achieve the required overall density. This weighting component is preferably constructed as a solid metal block, for example EP-A-0,333,311, EP-A-0,149,510, EP-A-0,062,391, or as a cylinder, for example EP-A-0,164,241 and Vet. Parasitology 12 (1983) 223-232. These metal components described in the literature have the disadvantage that they are not biodegradable and remain as foreign bodies in the stomach of the animal over the desired administration period. Disadvantageous consequences of this are, inter alia, interactions with other bolus systems in the case of repeated administration, irritations of the raucous membranes and problems with slaughtering and cutting up the animals.

The use of degradable weighting components, such as described in EP-A-0,332,094, represents a definite step toward overcoming these disadvantages. However, the systems described therein are also still not optimally suitable. They are composed of several completely different components. These components are, inter alia, a) a mixture (matrix) of a degradable polymer and active substance, b) a mixture (matrix) of a degradable polymer and particles of high density, c) a degradable polymer and d) particles of high density.

The complicated building-up of systems which as a rule makes necessary separate preparation and subsequent combination of the individual parts is disadvantageous. The maximum amount of active substance to be administered is greatly restricted by the limited volume of the degradable polymer. It additionally has to be taken into account that separation of the individual parts of the system can take place owing to degradation of the various polymers or owing to mechanical influences in the gastrointestinal tract. The bolus systems described therefore only satisfy with restrictions the practical requirements in preparation and therapeutic safety.

Finally, inter alia, bolus systems which are constructed from molded articles which, in addition to the active substance, contain iron granules and graphite and also a coating of magnesium alloy and a protective coating of non-degradable synthetic material are described in EP-A-0,243,111. Magnesium, iron and graphite form a galvanic element in gastric juice, which causes the corrosion of the magnesium coating. The release of active substance is controlled in this manner.

A disadvantage of this system is the simultaneous release of magnesium ions. Magnesium is a physiologically active substance and is employed in veterinary medicine as a pharmaceutical, for example against grass tetany in calves.

The production of the abovementioned bolus systems is comparatively complicated and cost-intensive. The pressing of the iron granules to give the molded articles causes a considerable abrasion of the pressing tools used. The short tool lives resulting from this lead to an increase in the production costs. The use of a non-degradable synthetic material is not unproblematical, as the synthetic material remains in the animal as a foreign body after the end of the period of action of the bolus or else is excreted and pollutes the environment.

A practical bolus system should meet the following requirements:
1) simple, safe administrability,
2) complete retention at the site of action during the entire duration of active substance release,
3) controlled active substance release with a clear end point,
4) no undesired side effects and no tissue damage,
5) no remaining foreign bodies after conclusion of the treatment.

These requirements are, surprisingly, met by a bolus system in which the bolus preparation is composed of the active substance, a non-water-soluble paraffin or wax, a substance which affects the mechanical properties of the preparation, in particular abrasion and/or disintegration, and optionally a surface-active substance and a powdered substance of high density (>3 g/cm³).

The invention therefore relates to a bolus preparation for oral administration in ruminants, containing 0.001 to 75% by weight, preferably up to 50% by weight, in particular up to 30% by weight, of at least one active substance, 3 to 75% by weight, preferably 5 to 60% by weight, in particular 5-50% by weight, of wax, 25 to 90% by weight, preferably 30-85% by weight, in particular 40-80% by weight, of powdered weighting agent and 0 to 30% by weight, preferably 0-14% by weight, in particular 0-10% by weight, of at least one physiologically tolerable sugar, sugar alcohol, water-soluble cellulose ether or polyethylene glycol, or mixture thereof.

If an active substance is not water-soluble or only water-soluble to a slight extent (such as, for example, fenbendazole), it is advantageous not to reduce the content of sugar, sugar alcohol, water-soluble cellulose ether or polyethylene glycol below 1% by weight. A content of 1.5 to 27% by weight, in particular 2 to 25% by weight, is then preferred.

The preparation may additionally also contain up to 8% by weight, preferably up to 6% by weight, of a surface-active substance, up to 10% by weight, preferably up to 6% by weight, of mold release agent, a lubricant and/or substances which affect the properties of the preparation.

Ruminants are understood as meaning, in particular, cattle, sheep and goats.

The therapeutic active substances are in particular compositions for controlling parasitic infections and/or diseases, for supplying deficient substances, and for controlling metabolic processes or for controlling endocrine processes.

According to the invention, for example the therapeutically active substance groups and compounds mentioned below can be employed in the bolus preparations.

Glucocorticoids for induction of birth, for example dexamethasone, betamethasone, flumethasone, and their esters and derivatives, gestagens for synchronization of estrus and estrus suppression, β₂-idrenergics for the treatment and prophylaxis of respiratory diseases, for preventing abortion and birth, for promoting growth and influencing metabolism, such as, for example, clenbuterol, ethyl 4-(2-tert-butylamino-l-hydroxyethyl)-2-cyano-6-fluorophenyl-carbamate hydrochloride, α[[[3-(1-benzimidazolyl)-1,1-dimethylpropyl]amino]methyl]-2-fluoro-4-hydroxybenzyl alcohol methanesulfonate monohydrate (cimaterol), 1-(4-amino-3-cyanophenyl)-2-isopropylaminoethanol, β-blockers for reducing transport stress, α₂-adrenergics against enteric diseases and for the treatment of hypoglycemic conditions, and also for sedation (for example clonidine, 2-[2-bromo-6-fluorophenylimino]imidazolidine), benzodiazepines and derivatives, such as, for example, brotizolam for sedation, anti-inflammatories for anti-inflammatory therapy, for example meloxicam, endorphins for stimulating voluntary movement of the rumen, steroid hormones (natural and synthetic) for promoting growth, for example oestradiol, progesterone and its esters and synthetic derivatives such as, for example, trenbolone, antiparasitics for controlling endo- and ectoparasites, such as, for example, levamisole, avermectin, benzimidazoles, pyrantel, morantel, febantel, cardio- and circulatory-active substances, for example etilefrin or pimobendan.

Preferred active substances are those from the group comprising benzimidazole and benzothiazole derivatives or the probenzimidazoles, in particular compounds of the formula I, II or III

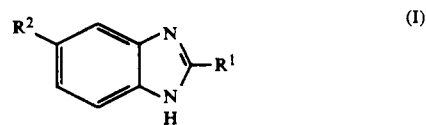

Ia), in which
$R^1$ is methoxycarbonylamino and
$R^2$ is n-propylmercapto (albendazole), phenylmercapto (fenbendazole), phenylsulfinyl (oxfendazole), benzoyl (mebendazole), p-fluorobenzoyl (flubendazole), p-fluorophenylsulfonyloxy (luxabendazole), cyclopropylcarbonyl (cyclobendazole) n-butyl (parbendazole), n-propoxy (oxibendazole) or H (carbendazime) or Ib), in which
$R^1$ is 4-thiazolyl and
$R^2$ is H (thiabendazole) or isopropoxycarbonylamino (cambendazole).

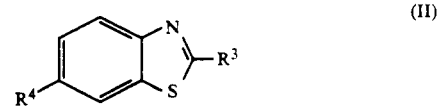

in which
$R^3$ is methoxycarbonylamino and
$R^4$ is n-propoxy (tioxidazole).

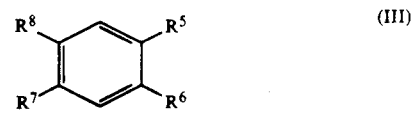

in which
$R^5$ is —N=C(NHCOCH₃)₂,
$R^6$ is —NHCOCH₂CH₃,
$R^7$ is phenylmercapto and
$R^8$ is H (febantel); or
$R^5$ is

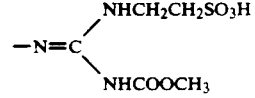

$R^6$ is NO₂, $R^7$ is H and $R^8$ is n-propylmercapto (netobimin); or $R^5$ and $R^6$ are each —NHCSNH—COOC₂H₅, $R^7$ and $R^8$ are each H (thiophanate).

Fenbendazole is particularly preferred.

To improve the growth and food utilization in ruminants, for example the substance groups and compounds mentioned below can be employed in the bolus preparations according to the invention.

Salinomycin, flavophospholipol, monensin, dehydromethylmonensin, narsin, desoxynarsin, lasalocid A, alborixin lysocellin, nigericin, dehydroxymethylnigericin, dianemycin, ionomycin, norbitomycin, and other polyether antibiotics, avoparcin, spiramycin, tylosin, virginiamycin, bacitracin A, carbadox, nitrovin, olaquindox, amprolium, arpinacid, dinitolmide, halofuginone, metichlorpindol, nicarbazin, decoquinate, triazine derivatives and the salts of said compounds such as salinomycin Na, monensin Na, tylosin phosphate, Zn bacitracin A, lasalocid A Na.

Phosphoglycolipids are particularly preferred, in particular flavophospholinol, salinomycin and its salts, preferably the Na salt.

A wax in the sense of the present invention is understood as meaning a physiologically acceptable naturally or artificially obtained substance which has the following properties: strong to brittle hard at room temperature, coarse to fine crystalline, translucent to opaque, but not glassy; melting without decomposition above 40° C., already of comparatively low viscosity and non-stringy a little above the melting point, strongly temperature-dependent consistency and solubility.

They differ from similar synthetic or natural products (for example resins, plastic materials) mainly in that, as a rule, they melt between about 50° and 90° C. Suitable waxes are, for example, recent waxes, such as candelilla and carnauba wax, and fossil waxes such as montan wax etc., mineral waxes such as ceresin and ozocerite (mineral wax), petrolatum, paraffin waxes and microwaxes; chemically modified waxes are, for example, the Hoechst and BASF waxes produced by oxidation of crude montan wax and hydrogenated jojoba oil or castor oil (for example Cutina HR) and also synthetic waxes.

With respect to its specific density, its composition and its amount, the powdered weighting agent is to be selected such that the bolus system remains in the stomach in spite of natural regurgitation. Depending on the size of the bolus system and its surface area, the specific density, depending on the composition of the density-imparting component, is in general greater than 3.0 g/cm$^3$, preferably greater than 4.0 g/cm$^3$.

Upwardly, the density is not a restricting criterion.

Weighting agents which have an adequately high density are listed by way of example:

| Weighting agent | Density (g/cm$^3$) |
| --- | --- |
| Silver | 10.5 |
| Copper | 8.9 |
| Iron | 7.8 |
| Nickel | 8.9 |
| Lead | 11.3 |
| Antimony | 6.7 |
| Tin | 7.3 |
| Zinc | 7.1 |
| Hydroxyapatite | 3.1–3.3 |
| Barium sulfate | 4.5 |
| Iron oxides | 5.2–5.7 |
| Barium titanate | 6.1 |
| Alumina | 4.0 |
| Tin oxide | 7.0 |
| Titanium dioxide (rutile) | 4.2 |
| Scheelite (calcium tungstate) | 6.1 |
| Ferberite (iron tungstate) | 7.2 |
| Fayalite (iron silicate) | 4.4 |
| Hercynite (iron aluminum oxide) | 4.3 |
| Powellite (calcium molybdate) | 4.3 |
| Calcium phosphates | 4.3 |

Non-toxic substances, such as barium sulfate or iron powder, in particular iron powder, are preferably employed.

In the case of substances or high specific density, particle sizes of less than 1 mm, possibly even less than 0.1 mm, are preferred. Thus, in the iron powder used according to the invention 97% of the particles are $\leq 0.15$ mm, $80\% \leq 0.1$ mm.

In the case of water-soluble active substances, the content of sugar, sugar alcohol, water-soluble cellulose ether or polyethylene glycol can be reduced, or these auxiliaries can be left out completely.

Suitable sugars according to the invention are, for example, water-soluble pharmaceutically acceptable monosaccharides and disaccharides. Lactose is preferred, but glucose, fructose, xylose, galactose, sucrose, maltose and related compounds such as mannitol, xylitol and sorbitol are also suitable.

Suitable water-soluble cellulose ethers are the ®Tylose brands ®Tylose MB (methylcellulose) and ®Tylose H (hydroxyethylcellulose); methylcellulose is preferred.

Polyethylene glycols (PEGS) in the sense of the present invention are, for example, PEG 400, 600, 1500, 2000, 3000, 4000, 6000 and 10000. The solid types are preferred.

Suitable surface-active substances are preferably physiologically tolerable nonionic surfactants having an HLB between 10 and 20, in particular the polyoxyethylene sorbitan esters, such as the monolaurate (®Tween 20), the monopalmitate (®Tween 40) and the monostearate (®Tween 60). ®Tween 20 is preferred.

Lubricants and mold release agents customarily employed are talc, stearates or other metal soaps, such as fumarates or palmitates, preferably magnesium stearate.

The auxiliary which can influence the mechanical properties, in particular abrasion and disintegration, is customarily highly disperse silica (®Aerosil).

The invention furthermore relates to molded articles for oral administration in ruminants composed of a composition defined above, which contains an adequate amount of the active substance for defined release during a fixed period, and optionally a coating which is soluble or degradable in the digestive tract.

The molded articles can be prepared as a melt of the paraffin or wax in which the other constituents are dissolved or suspended. The melt is then poured into a mold and solidified therein.

Another preferred method is to prepare fused granules in a suitable mixer. The granules can then be pressed in a press to give the desired molded article. In both cases, a matrix is formed in which the active substance is embedded and released with a delay. The preparation processes described have the advantage, in comparison with the preparation processes known hitherto for bolus systems, of being very inexpensive as processes and equipment which exist and are approved for pharmaceutical preparation can be employed. The cost factor is of substantial importance in the context of industrial series production.

Figure 2:
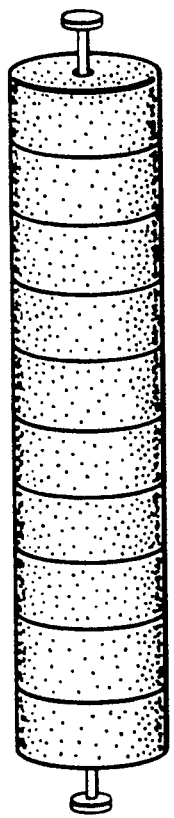

Depending on the animal species, the bolus or the individual tablets have a diameter which is between 1 cm and 4 cm. The total length of the bolus should not exceed 12 cm; the lower limit is a single tablet. The bolus can be composed of one piece (FIG. 1) or any desired number of individual pieces (for example tablets) (FIGS. 2 and 3).

The total volume may thus be between about 0.5 and 200 cm$^3$.

By increase the surface area, i.e. by conversion of a piece (FIG. 1) to the tablet form (FIG. 2, 3), the release rate can be increased with the same composition of the matrix and suited to the requirements depending on the number, size and shape of the tablets. The loss of single tablets during the treatment time, for example by regurgitation, is prevented by connecting the tablets to one another. This connection can be carried out in a flexible manner, for example by means of a tape, a thread or a chain, in an elastic manner or rigidly, for example by means of a rod (FIG. 2, 3). The connecting material may be made, for example, of physiologically acceptable synthetic material (for example silicone) or of a physiologically acceptable material which is degraded in the intestine.

A tablet bolus (FIG. 2, 3) moreover avoids the risk that the matrix may be destroyed or damaged by external action. A more uniform release during the entire administration period is thus ensured.

The thickness of the tablets can be varied depending on the desired release profile of the active substance. Various tablet shapes, for example biplanar or biconvex, are also possible. Tablets of different thickness and shape can also be combined with one another in one bolus. It is also possible to combine with one another tablets which are loaded with one active substance in a varying concentration or with different active substances. To facilitate administration, the tablets connected with one another can be stuck together with the aid of a water-soluble adhesive or surrounded with a coating which is soluble or can be degraded in the digestive tract. The material of the adhesive or of the coating may be composed, for example, of cellulose and cellulose derivatives, gelatin and other suitable polymers and copolymers. The tablets can also be surrounded by a net.

The products prepared in the abovementioned manner can be composed of up to 30, preferably up to 20, in particular up to 10, molded articles. The matrix is completely degraded during the treatment period; no residue remains after conclusion of the treatment.

The active substance release system described is basically suitable for the administration of all active substances which are administered over a relatively long period in the veterinary medicine and animal nutrition areas. Different physical properties of the active substances, for example solubility differences, can be influenced by suitable additives which control the release of active substances. Suitable additives for controlling the release profile in accordance with the therapeutic requirements are known to the person skilled in the art.

The invention therefore also relates to the use of the abovementioned molded articles and products in ruminants for the prophylaxis and/or treatment of diseases and for influencing growth, metabolism, body weight, tissue composition and/or feed utilization.

The examples below serve to illustrate the invention without it being restricted thereto.

A. General preparation example for a melt

The wax (for example Hoechst Wax E or hydrogenated castor oil, such as Cutina HR) is melted in a vessel (temperature about 80°-100°C.). The active substance, the weighting agent (for example iron powder) and the other auxiliaries are added with stirring.

The viscous melt is transferred to suitable warmed molds and slowly cooled to room temperature.

B. General preparation example for fused granules

The constituents of the formulation are weighed into a suitable mixer (for example a Henschel fluid mixer). The heat generated during mixing due to friction leads to formation of fused granules. After cooling the granules to room temperature, agglomerates are comminuted by passing through a sieve (for example Frewitt granulator, mesh width: 1 mm).

The granules standardized in this way are pressed to give the desired molded articles using a press. If necessary, a lubricant or mold release agent can be added.

The preparations prepared according to A. or B. in the following examples preferably have the following composition (% data are % by weight):

Active substance: up to 30%
Wax: 5-50%
Iron: 40-80%
Lactose, methylcellulose or polyethylene glycol: 0-25%
Highly disperse silica: up to 2%
Polyoxyethylene sorbitan monolaurate: up to 6%
Mg stearate: up to 6%.

Examples

|  | No. | | | | | | | |
|---|---|---|---|---|---|---|---|---|
|  | 1 | 2 | 3 | 4 | 5 | 6 | 7 | 8 |
| ®Flavomycin | 5% | 10% | 25% | 10% | 10% | 10% | 10% | 10% |
| Hoechst Wax E | 45% | 20% | 30% | — | 25% | 30% | 20% | 30% |
| ®Cutina HR | — | — | — | 20% | — | — | — | — |
| Iron | 50% | 70% | 45% | 70% | 60% | 55% | 67% | 59% |
| Lactose |  |  |  |  | 5% |  |  |  |
| Methylcellulose |  |  |  |  |  | 5% |  |  |
| ®Tween 20 |  |  |  |  |  |  | 3% |  |
| ®Aerosil |  |  |  |  |  |  |  | 1% |

|  | No. | | | | | | |
|---|---|---|---|---|---|---|---|
|  | 9 | 10 | 11 | 12 | 13 | 14 | 15 |
| ®Flavomycin | 10% | 10% | 10% | 10% | 10% | 10% | 10% |
| Hoechst Wax E | 17.5% | 17.5% | 15% | 12.5% | 15% | 15% | 15% |
| Iron | 70% | 70% | 70% | 70% | 70% | 70% | 65% |
| PEG 400 | 2.5% | — | — | — | — | — | — |
| PEG 2000 | — | 2.5% | 5% | 7.5% | 2.5% | — | — |
| PEG 6000 | — | — | — | — | — | 5% | 10% |
| Mg Stearate | — | — | — | — | 2.5% | — | — |

-continued

|  | No. | | | | | |
|---|---|---|---|---|---|---|
|  | 16 | 17 | 18 | 19 | 20 | 21 |
| ®Flavomycin | 12% | 15% | 15% | 10% | 15% | 10% |
| Hoechst Wax E | 12.5% | 9.5% | 10% | 15% | 15% | 20% |
| Iron | 70% | 70% | 65% | — | 64% | 65% |
| Barium sulfate | — | — | — | 70% | — | — |
| PEG 2000 | 5.5% | 5.5% | 5% | 5% | — | — |
| Mg Stearate | — | — | 5% | — | 6% | 5% |

Salinomycin Na-containing preparations are prepared in an analogous manner.

|  | No. | | | | | | | |
|---|---|---|---|---|---|---|---|---|
|  | 22 | 23 | 24 | 25 | 26 | 27 | 28 | 29 |
| Fenbendazole | 5% | 10% | 25% | 10% | 10% | 10% | 10% | 10% |
| Hoechst Wax E | 45% | 20% | 30% | — | 20% | 30% | 20% | 30% |
| ®Cutina HR | — | — | — | 20% | — | — | — | — |
| Iron | 50% | 70% | 45% | 70% | 60% | 50% | 67% | 59% |
| Lactose | | | | | 10% | | | |
| Methylcellulose | | | | | | 10% | | |
| ®Tween 20 | | | | | | | 3% | |
| ®Aerosil | | | | | | | | 1% |

|  | No. | | | | | | |
|---|---|---|---|---|---|---|---|
|  | 30 | 31 | 32 | 33 | 34 | 35 | 36 |
| Fenbendazole | 10% | 10% | 10% | 10% | 10% | 10% | 10% |
| Hoechst Wax E | 17.5% | 17.5% | 15% | 12.5% | 15% | 15% | 10% |
| Iron | 70% | 70% | 70% | 70% | 70% | 70% | 65% |
| PEG 400 | 2.5% | — | — | — | — | — | — |
| PEG 2000 | — | 2.5% | 5% | 7.5% | 2.5% | — | — |
| PEG 6000 | — | — | — | — | — | 5% | 15% |
| Mg Stearate | — | — | — | — | 2.5% | — | — |

|  | No. | | | |
|---|---|---|---|---|
|  | 37 | 38 | 39 | 40 |
| Fenbendazole | 12% | 15% | 15% | 10% |
| Hoechst Wax E | 12.5% | 9.5% | 10% | 15% |
| Iron | 70% | 70% | 65% | — |
| Barium sulfate | — | — | — | 70% |
| PEG 2000 | 5.5% | 5.5% | 5% | 5% |
| Mg Stearate | — | — | 5% | — |

If the wax content is below 20%, the melt is highly viscous and the processing is critical; with wax contents of ≦10%, the melt process cannot be used.

We claim:

1. A composition of fused granules for oral administration in ruminants, containing 0.001 to 75% by weight of at least one therapeutically active substance, 3 to 75% by weight of wax, 25 to 90% by weight of powdered weighting agent and 0 to 30% by weight of at least one physiologically tolerable sugar, sugar alcohol, water-soluble cellulose ether or polyethylene glycol.

2. A composition as in claim 1, additionally containing at least one substance selected from the group consisting of a surface-active substance, a lubricant, a mold release agent and a substance which affects the mechanical properties of the composition.

3. A composition as claimed in claim 1, wherein the weighting agent is iron powder.

4. A composition as claimed in claim 1, wherein the therapeutically active substance is a substance selected from the group consisting of an agent for the control of parasitic infections, an agent for the control of parasitic diseases, an agent for the supply of deficient substances, an agent for the control of metabolic processes, and an agent for the control of endocrine processes.

5. A composition as claimed in claim 1, wherein the therapeutically active substance is a substance for improving growth or the utilization of feed.

6. A composition as claimed in claim 5, wherein the therapeutically active substance is a polyether antibiotic.

7. A composition as claimed in claim 5, wherein the therapeutically active substance is a phosphoglycolipid.

8. A composition as claimed in claim 7, wherein the therapeutically active substance is flavophospholipol.

9. A composition as claimed in claim 5, wherein the therapeutically active substance salinomycin or its salt.

10. A composition as claimed in claim 1, wherein the therapeutically active substance is an anthelmintic.

11. A composition as claimed in claim 10, wherein the anthelmintic is selected from group consisting of benzimidazole, benzothiazole derivatives, and probenzimidazoles.

12. A composition as claimed in claim 11, wherein the therapeutically active substance fenbendazole.

13. A molded article for oral administration in ruminants, composed of a composition as claimed in claim 1, which contains an adequate amount of the therapeutically active substance for defined release during a fixed period, and optionally a coating which is soluble or can be degraded in the digestive tract.

14. A product containing a plurality of molded articles as claimed in claim 13.

15. A product as claimed in claim 14, wherein the molded articles are connected to one another by mean of a tape, a thread, a chain, a rod, or by bonding or inclusion in a net.

16. A product as claimed in claim 14, which is composed of molded articles of varying dimension and shape, a different content of the therapeutically active substance or a different type of the therapeutically active substance.

17. A product as claimed in claim 14, whose total volume is between 0.5 and 200 cm³.

18. A method for the treatment of diseases in ruminants, which are caused by helminths, which comprises administration of an effective amount of at least one active substance selected from the therapeutically active substance group consisting of benzimidazole, benzothiazole derivatives and probenzimidazoles, in the form of a molded article as claimed in claim 13 or of a product as claimed in claim 14.

19. A method for affecting growth, metabolism, body weight, tissue composition or feed utilization, which comprises administration of a molded article as claimed in claim 13 or of a product as claimed in claim 14.

20. The method as claimed in claim 19 for influencing growth or feed utilization.

21. A method for the prophylaxis of diseases in ruminants, which are caused by helminths, which comprises administration of an effective amount of at least one active substance selected from the therapeutically active substance group consisting of benzimidazole, benzothiazole derivatives and probenzimidazoles, in the form of a molded article as claimed in claim 13 or of a product as claimed in claim 14.

22. A process for the preparation of a composition of fused granules for oral administration in ruminants containing 0.001 to 75% by weight of at least one therapeutically active substance, 3 to 75% by weight of wax, 25 to 90% by weight of powdered weighting agent and 0 to 30% by weight of at least one physiologically tolerable sugar, sugar alcohol, water-soluble cellulose ether or polyethylene glycol, said process comprising:
   a) melting the wax and stirring into the molten wax the therapeutically active substance, the weighing agent and, if present, the at least one physiologically tolerable sugar, sugar alcohol, water-soluble cellulose ether or polyethylene glycol; or
   b) preparing fused granules from the therapeutically active substance, the wax, the weighting agent and, if present, the at least one physiologically tolerable sugar, sugar alcohol, water-soluble cellulose ether or polyethylene glycol, in a suitable mixer.

23. A process for the preparation of a molded article for oral administration in ruminants, composed of a composition of fused granules for oral administration in ruminants containing 0.001 to 75% by weight of at least one therapeutically active substance, 3 to 75% by weight of wax, 25 to 90% by weight of powdered weighting agent and 0 to 30% by weight of at least one physiologically tolerable sugar, sugar alcohol, water-soluble cellulose ether or polyethylene glycol, said molded article also containing an adequate amount of the therapeutically active substance for defined release during a fixed period and, optionally a coating which is soluble or can be degraded in the digestive tract, said process comprising:
   a) preparing a melt by stirring the therapeutically active substance, the weighting agent and, if present, the at least one physiologically tolerable sugar, sugar alcohol, water-soluble cellulose ether or polyethylene glycol into molten wax, transferring the melt to a suitable warmed mold and allowing the transferred melt to cool to give the molded article, or,
   b) preparing fused granules from the therapeutically active substance, the wax, the weighting agent and, if present, the at least one physiologically tolerable sugar, sugar alcohol, water-soluble cellulose ether or polyethylene glycol, in a suitable mixer, comminuting and pressing the fused granules in a press to give the molded article; and
   optionally coating the molded article obtained from a) or b) with a coating which is soluble or can be degraded in the digestive tract.

24. A composition for oral administration in ruminants, containing 0.001 to 75% by weight of at least one therapeutically active substance, which is not water-soluble or only water-soluble to a slight extent; 3 to 75% by weight of wax, 25 to 90% by weight of at least one iron powder, 97% of which is particles of at least 0.15 mm; and 1 to 30% by weight of at least one physiologically tolerable sugar, sugar alcohol, water-soluble cellulose ether or polyethylene glycol.

25. A composition as claimed in claim 24, additionally containing at least one substance selected from the group consisting of a surface-active substance, a lubricant, a mold release agent and a substance which affects the mechanical properties of the composition.

26. A composition as claimed in claim 24, wherein the therapeutically active substance is a substance selected from the group consisting of an agent for the control of parasitic infections, an agent for the control of parasitic diseases, an agent for the supply of deficient substances, and agent for the control of metabolic processes, and an agent for the control of endocrine processes.

27. A composition as claimed in claim 24, wherein the therapeutically active substance is a substance for improving growth or the utilization of feed.

28. A composition as claimed in claim 24, wherein the therapeutically active substance is an anthelmintic.

29. A composition as claimed in claim 28, wherein the anthelmintic is selected from the group consisting of benzimidazole, benzolthlazole derivatives, and the probenzimidazoles.

30. A composition as claimed in claim 29, containing the therapeutically active substance fenbendazole.

31. A molded article for oral administration in ruminants, composed of a composition as claimed in claim 24, which contains an adequate amount of the therapeutically active substance for defined release during a fixed period, and optionally a coating which is soluble or can be degraded in the digestive tract.

32. A product containing a plurality of molded articles as claimed in claim 31.

33. A product as claimed in claim 32, wherein the molded articles are connected to one another by means of a tape, a thread, a chain, a rod, or by bonding or inclusion in a net.

34. A product as claimed in claim 32, which is composed of molded articles of varying dimension and shape, a different content of the therapeutically active substance or different type of the therapeutically active substance.

35. A product as claimed in claim 32, whose total volume is between 0.5 and 200 cm³.

36. A method for the treatment of diseases in ruminants, which are caused by helminths, which comprises administration of an effective amount of at least one active substance selected from the therapeutically active substance group consisting of benzimidazole, benzothiazole derivatives and probenzimidazoles, in the form of a molded article as claimed in claim 31 or of a product as claimed in claim 32.

37. A method for the prophylaxis of diseases in ruminants, which are caused by helminths, ruminants, which comprises administration of an effective amount of at least one active substance selected from the therapeutically active substance group consisting of benzimidazole, benzothiazole derivatives and probenzimidazoles, in the form of a molded article as claimed in claim 31 or of a product as claimed in claim 32.

38. A method for affecting growth, metabolism, body weight, tissue composition or feed utilization, which comprises administration of a molded article as claimed in claim 31 or of a product as claimed in claim 32.

39. The method as claimed in claim 38 for influencing growth or feed utilization.

40. A process for the preparation of a composition for oral administration in ruminants, containing 0.001 to 75% by weight of at least one therapeutically active substance which is not water-soluble or only water-soluble to a slight extent, 3 to 75% by weight of wax, 25 to 90% by weight of a weighting agent which is at least one iron powder 97% of which is particles of a size $\leq 0.15$ mm, and 1 to 30% by weight of at least one physiologically tolerable sugar, sugar alcohol, water-soluble cellulose ether or polyethylene glycol, said process comprising a) melting the wax and stirring into the molten wax the therapeutically active substance, the weighting agent and, the at least one physiologically tolerable sugar, sugar alcohol, water-soluble cellulose ether or polyethylene glycol; or b) preparing fused granules from the therapeutically active substance, the wax, the weighting agent and, the at least one physiologically tolerable sugar, sugar alcohol, water-soluble cellulose ether or polyethylene glycol, in a suitable mixer.

41. A process for the preparation of a molded article for oral administration in ruminants composed of a composition for oral administration in ruminants containing 0.001 to 75% by weight of at least one therapeutically active substance which is not water-soluble or only water-soluble to a slight extent, 3 to 75% by weight of wax, 25 to 90% by weight of a weighting agent which is at least one iron powder 97% of which is particles of a size $\leq 0.15$ mm, and 1 to 30% by weight of at least one physiologically tolerable sugar, sugar alcohol, water-soluble cellulose ether or polyethylene glycol, said molded article also containing an adequate amount of the therapeutically active substance for defined release during a fixed period, and optionally a coating which is soluble or can be degraded in the digestive tract, said process comprising:

a) preparing a melt by stirring the therapeutically active substance, the weighting agent, and, the at least one physiologically tolerable sugar, sugar alcohol, water-soluble ether or polyethylene glycol into molten wax, transferring the melt to a suitable warmed mold and allowing the transferred melt to cool to give the molded article, or, b) preparing fused granules from the therapeutically active substance, the wax, the weighting agent and, the at least one physiologically tolerable sugar, sugar alcohol, water-soluble cellulose ether or polyethylene glycol, in a suitable mixer, comminuting and pressing the fused granules in a press to give the molded article; and optionally coating the molded article obtained from a) or b) with a coating which is soluble or can be degraded in the digestive tract.

* * * * *